US009447005B2

(12) United States Patent
Hale et al.

(10) Patent No.: US 9,447,005 B2
(45) Date of Patent: Sep. 20, 2016

(54) PROCESSES FOR PRODUCING ANHYDROUS ETHANOL COMPOSITIONS (71) Applicant: Celanese International Corporation, Irving, TX (US)

(72) Inventors: Trinity Horton Hale, Houston, TX (US); Radmila Wollrab, Pasadena, TX (US); Victor J. Johnston, Houston, TX (US); Lincoln Sarager, Houston, TX (US); R. Jay Warner, Houston, TX (US); Gerald Grusendorf, Rosharon, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 197 days.

(21) Appl. No.: 13/969,813

(22) Filed: Aug. 19, 2013

(65) Prior Publication Data

US 2013/0331619 A1 Dec. 12, 2013

Related U.S. Application Data (62) Division of application No. 12/903,756, filed on Oct. 13, 2010, now Pat. No. 8,541,633.

(60) Provisional application No. 61/332,726, filed on May 7, 2010, provisional application No. 61/300,815, filed on Feb. 2, 2010.

(51) Int. Cl.
  *C07C 29/152* (2006.01)
  *C07C 29/149* (2006.01)
  (Continued)

(52) U.S. Cl.
  CPC .......... *C07C 29/152* (2013.01); *C07C 29/149* (2013.01); *C07C 29/76* (2013.01); *C07C 29/84* (2013.01)

(58) Field of Classification Search
  CPC .................................................. C07C 29/152
  USPC ........................... 422/187; 568/885; 585/250
  See application file for complete search history.

(56) References Cited

U.S. PATENT DOCUMENTS 1,939,116 A  12/1933  Fuchs
2,105,540 A  1/1938  Lazier
(Continued)

FOREIGN PATENT DOCUMENTS

CN  1230458  10/1999
CN  201768393  3/2011
(Continued)

OTHER PUBLICATIONS

"Solvent Screening Study and Conceptual Extractive Distillation Process to Produce Anhydrous Ethanol from Fermentation Broth" Fu-Ming Lee and Robert H. Pahl—Ind. Eng. Chem. Process Des. Dev. 1985, 24, 168-172.*
(Continued)

*Primary Examiner* — Huy-Tram Nguyen
(74) *Attorney, Agent, or Firm* — Kilpatrick Townsend & Stockton LLP (57) ABSTRACT

The present invention is to a process for producing a anhydrous ethanol composition comprising hydrogenating acetic acid in the presence of a catalyst to form a crude ethanol product; separating in a first column at least a portion of the crude ethanol product into a first distillate comprising ethanol, water and ethyl acetate, and a first residue comprising acetic acid; separating in a second column at least a portion of the first distillate into a second distillate comprising ethyl acetate and a second residue comprising ethanol and water; separating in a third column at least a portion of the second residue into a third distillate comprising ethanol and residual water and a third residue comprising separated water; and dehydrating at least a portion of the third distillate to form the anhydrous ethanol composition. The anhydrous ethanol composition, as formed, comprises less than 1 wt. % water.

19 Claims, 2 Drawing Sheets (51) Int. Cl.
*C07C 29/76* (2006.01)
*C07C 29/84* (2006.01)

(56) References Cited

U.S. PATENT DOCUMENTS

| | | | |
|---|---|---|---|
| 2,192,137 A | 2/1940 | Kvalnes | |
| 2,549,416 A | 4/1951 | Brooks | |
| 2,607,807 A | 8/1952 | Ford | |
| 2,649,407 A | 8/1953 | Harrison et al. | |
| 2,702,783 A | 2/1955 | Harrison et al. | |
| 2,744,939 A | 5/1956 | Kennel | |
| 2,801,209 A | 7/1957 | Muller et al. | |
| 2,882,244 A | 4/1959 | Milton | |
| 3,102,150 A | 8/1963 | Hunter et al. | |
| 3,130,007 A | 4/1964 | Breck | |
| 3,408,267 A | 10/1968 | Miller et al. | |
| 3,445,345 A | 5/1969 | Katzen et al. | |
| 3,478,112 A | 11/1969 | Adam et al. | |
| 3,702,886 A | 11/1972 | Argauer et al. | |
| 3,729,429 A | 4/1973 | Robson | |
| 3,769,329 A | 10/1973 | Knox et al. | |
| 3,847,756 A | 11/1974 | Statman et al. | |
| 3,953,524 A | 4/1976 | Steiner | |
| 3,990,952 A | 11/1976 | Katzen et al. | |
| 4,052,467 A | 10/1977 | Mills et al. | |
| 4,065,512 A | 12/1977 | Cares | |
| 4,270,015 A | 5/1981 | Knifton et al. | |
| 4,275,228 A | 6/1981 | Gruffaz et al. | |
| 4,306,942 A | 12/1981 | Brush et al. | |
| 4,317,918 A | 3/1982 | Takano et al. | |
| 4,319,058 A | 3/1982 | Kulprathipanja et al. | |
| 4,328,373 A | 5/1982 | Strojny | |
| 4,337,351 A | 6/1982 | Larkins | |
| 4,379,028 A | 4/1983 | Berg et al. | |
| 4,395,576 A | 7/1983 | Kwantes et al. | |
| 4,398,039 A | 8/1983 | Pesa et al. | |
| 4,399,305 A | 8/1983 | Schreck et al. | |
| 4,421,939 A | 12/1983 | Kiff et al. | |
| 4,422,903 A | 12/1983 | Messick et al. | |
| 4,426,541 A | 1/1984 | King | |
| 4,443,639 A | 4/1984 | Pesa et al. | |
| 4,451,677 A | 5/1984 | Bradley et al. | |
| 4,454,358 A | 6/1984 | Kummer et al. | |
| 4,465,854 A | 8/1984 | Pond et al. | |
| 4,465,875 A * | 8/1984 | Greenbank et al. | 568/916 |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,514,515 A | 4/1985 | Travers et al. | |
| 4,517,391 A * | 5/1985 | Schuster et al. | 568/885 |
| 4,520,213 A | 5/1985 | Victor | |
| 4,521,630 A | 6/1985 | Wattimena et al. | |
| 4,527,995 A | 7/1985 | Itow et al. | |
| 4,541,897 A | 9/1985 | Sommer et al. | |
| 4,550,185 A | 10/1985 | Mabry et al. | |
| 4,559,109 A | 12/1985 | Lee et al. | |
| 4,569,726 A * | 2/1986 | Berg et al. | 203/56 |
| 4,581,473 A | 4/1986 | Polichnowski et al. | |
| 4,592,806 A | 6/1986 | Ilgner et al. | |
| 4,613,700 A | 9/1986 | Maki et al. | |
| 4,626,321 A | 12/1986 | Grethlein et al. | |
| 4,626,604 A | 12/1986 | Hiles et al. | |
| 4,654,123 A | 3/1987 | Berg et al. | |
| 4,678,543 A | 7/1987 | Houben et al. | |
| 4,692,218 A | 9/1987 | Houben et al. | |
| 4,760,171 A | 7/1988 | Isogai et al. | |
| 4,762,817 A | 8/1988 | Logsdon et al. | |
| 4,777,303 A | 10/1988 | Kitson et al. | |
| 4,804,791 A | 2/1989 | Kitson et al. | |
| 4,826,795 A | 5/1989 | Kitson et al. | |
| 4,842,693 A | 6/1989 | Wheldon | |
| 4,876,402 A | 10/1989 | Logsdon et al. | |
| 4,886,905 A | 12/1989 | Larkins et al. | |
| 4,902,823 A | 2/1990 | Wunder et al. | |
| 4,961,826 A | 10/1990 | Grethlein et al. | |
| 4,978,778 A | 12/1990 | Isshiki et al. | |
| 4,985,572 A | 1/1991 | Kitson et al. | |
| 4,990,655 A | 2/1991 | Kitson et al. | |
| 4,994,608 A | 2/1991 | Torrence et al. | |
| 5,001,259 A | 3/1991 | Smith et al. | |
| 5,004,845 A | 4/1991 | Bradley et al. | |
| 5,008,235 A | 4/1991 | Wegman et al. | |
| 5,026,908 A | 6/1991 | Smith et al. | |
| 5,035,776 A | 7/1991 | Knapp | |
| 5,061,671 A | 10/1991 | Kitson et al. | |
| 5,070,016 A | 12/1991 | Hallberg et al. | |
| 5,093,534 A | 3/1992 | Ludwig et al. | |
| 5,124,004 A | 6/1992 | Grethlein et al. | |
| 5,137,861 A | 8/1992 | Shih et al. | |
| 5,144,068 A | 9/1992 | Smith et al. | |
| 5,149,680 A * | 9/1992 | Kitson et al. | 502/185 |
| 5,155,084 A | 10/1992 | Horn et al. | |
| 5,185,308 A | 2/1993 | Bartley et al. | |
| 5,185,481 A | 2/1993 | Muto et al. | |
| 5,206,434 A | 4/1993 | Scates et al. | |
| 5,215,902 A | 6/1993 | Tedder | |
| 5,233,099 A | 8/1993 | Tabata et al. | |
| 5,237,108 A | 8/1993 | Marraccini et al. | |
| 5,241,106 A | 8/1993 | Inoue et al. | |
| 5,243,095 A | 9/1993 | Roberts et al. | |
| 5,250,271 A | 10/1993 | Horizoe et al. | |
| 5,284,983 A | 2/1994 | Muto et al. | |
| 5,306,845 A | 4/1994 | Yokohama et al. | |
| 5,334,769 A | 8/1994 | Ferrero et al. | |
| 5,348,625 A | 9/1994 | Berg | |
| 5,350,504 A | 9/1994 | Dessau | |
| 5,399,752 A | 3/1995 | Okrasinski et al. | |
| 5,415,741 A | 5/1995 | Berg | |
| 5,426,246 A | 6/1995 | Nagahara et al. | |
| 5,437,770 A | 8/1995 | Berg | |
| 5,445,716 A | 8/1995 | Berg | |
| 5,449,440 A | 9/1995 | Rescalli et al. | |
| 5,475,144 A | 12/1995 | Watson et al. | |
| 5,475,182 A | 12/1995 | Janssen | |
| 5,476,827 A | 12/1995 | Ferrero et al. | |
| 5,480,665 A | 1/1996 | Smith | |
| 5,488,185 A | 1/1996 | Ramachandran et al. | |
| 5,502,248 A | 3/1996 | Funk et al. | |
| 5,527,969 A | 6/1996 | Kaufhold et al. | |
| 5,565,068 A | 10/1996 | Parker et al. | |
| RE35,377 E | 11/1996 | Steinberg et al. | |
| 5,585,523 A | 12/1996 | Weiguny et al. | |
| 5,599,976 A | 2/1997 | Scates et al. | |
| 5,663,430 A | 9/1997 | Morris et al. | |
| 5,720,784 A | 2/1998 | Killick et al. | |
| 5,762,765 A | 6/1998 | Berg | |
| 5,767,307 A | 6/1998 | Ramprasad et al. | |
| 5,770,770 A | 6/1998 | Kim et al. | |
| 5,800,681 A | 9/1998 | Berg | |
| 5,821,111 A | 10/1998 | Gaddy et al. | |
| 5,849,657 A | 12/1998 | Rotgerink et al. | |
| 5,858,031 A | 1/1999 | Perlman | |
| 5,861,530 A | 1/1999 | Atkins et al. | |
| 5,945,570 A | 8/1999 | Arhancet et al. | |
| 5,955,397 A | 9/1999 | Didillon et al. | |
| 5,973,193 A | 10/1999 | Crane et al. | |
| 5,993,610 A | 11/1999 | Berg | |
| 6,040,474 A | 3/2000 | Jobson et al. | |
| 6,049,008 A | 4/2000 | Roberts et al. | |
| 6,093,845 A | 7/2000 | Van Acker et al. | |
| 6,114,571 A | 9/2000 | Abel et al. | |
| 6,121,498 A * | 9/2000 | Tustin et al. | 568/420 |
| 6,140,535 A | 10/2000 | Williams | |
| 6,143,930 A | 11/2000 | Singh et al. | |
| 6,232,352 B1 | 5/2001 | Vidalin | |
| 6,232,491 B1 * | 5/2001 | Cunnington et al. | 560/248 |
| 6,232,504 B1 | 5/2001 | Barteau et al. | |
| 6,294,703 B1 | 9/2001 | Hara et al. | |
| 6,375,807 B1 | 4/2002 | Nieuwoudt et al. | |
| 6,462,231 B1 | 10/2002 | Yanagawa et al. | |
| 6,472,555 B2 | 10/2002 | Choudary et al. | |
| 6,486,366 B1 | 11/2002 | Ostgard et al. | |
| 6,495,730 B1 | 12/2002 | Konishi et al. | |

(56) References Cited

U.S. PATENT DOCUMENTS

| | | |
|---|---|---|
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,727,380 B2 | 4/2004 | Ellis et al. |
| 6,755,975 B2 | 6/2004 | Vane et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,297,236 B1 | 11/2007 | van der Griend |
| 7,351,559 B2 | 4/2008 | Verser et al. |
| 7,375,049 B2 | 5/2008 | Hayes et al. |
| 7,399,892 B2 | 7/2008 | Rix et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | van der Griend |
| 7,608,744 B1 | 10/2009 | Johnston et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,718,039 B2 | 5/2010 | Dirkzwager et al. |
| 7,732,173 B2 | 6/2010 | Mairal et al. |
| 7,744,727 B2 | 6/2010 | Blum et al. |
| 7,816,565 B2 | 10/2010 | Johnston et al. |
| 7,820,852 B2 | 10/2010 | Johnston et al. |
| 7,834,223 B2 | 11/2010 | Atkins |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,947,746 B2 | 5/2011 | Daniel et al. |
| 8,071,821 B2 | 12/2011 | Johnston et al. |
| 2003/0004057 A1 | 1/2003 | Yamaguchi et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bharadwaj et al. |
| 2004/0195084 A1 | 10/2004 | Hetherington et al. |
| 2005/0176996 A1 | 8/2005 | Law et al. |
| 2006/0019360 A1 | 1/2006 | Verser et al. |
| 2006/0102520 A1 | 5/2006 | Lapinski et al. |
| 2006/0127999 A1 | 6/2006 | Verser et al. |
| 2007/0031954 A1 | 2/2007 | Mairal et al. |
| 2007/0106246 A1 | 5/2007 | Modesitt |
| 2007/0138083 A1 | 6/2007 | Aizawa |
| 2007/0238906 A1 | 10/2007 | Brown et al. |
| 2007/0270511 A1 | 11/2007 | Melnichuk et al. |
| 2008/0135396 A1 | 6/2008 | Blum |
| 2008/0154071 A1* | 6/2008 | Husen et al. ............... 568/862 |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey |
| 2009/0209786 A1 | 8/2009 | Scates et al. |
| 2009/0221725 A1 | 9/2009 | Chorney et al. |
| 2009/0274480 A1 | 11/2009 | Zona |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0069514 A1 | 3/2010 | Gracey et al. |
| 2010/0069515 A1 | 3/2010 | Tirtowidjojo et al. |
| 2010/0113843 A1 | 5/2010 | Lee et al. |
| 2010/0121114 A1 | 5/2010 | Weiner et al. |
| 2010/0125148 A1 | 5/2010 | Johnston et al. |
| 2010/0137630 A1 | 6/2010 | Garton et al. |
| 2010/0168467 A1 | 7/2010 | Johnston et al. |
| 2010/0168493 A1 | 7/2010 | Le Peltier et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0249479 A1 | 9/2010 | Berg-Slot et al. |
| 2011/0004033 A1 | 1/2011 | Johnston et al. |
| 2011/0046421 A1 | 2/2011 | Daniel et al. |
| 2011/0071312 A1 | 3/2011 | Johnston et al. |
| 2011/0082322 A1 | 4/2011 | Jevtic et al. |
| 2011/0098501 A1 | 4/2011 | Johnston et al. |
| 2011/0190547 A1 | 8/2011 | Jevtic et al. |
| 2011/0190548 A1 | 8/2011 | Jevtic et al. |
| 2011/0275862 A1 | 11/2011 | Johnston et al. |

FOREIGN PATENT DOCUMENTS

| | | |
|---|---|---|
| CN | 102091429 | 6/2011 |
| CN | 102228831 | 11/2011 |
| CN | 102229520 | 11/2011 |
| CN | 101525272 | 5/2012 |
| EP | 0056488 | 7/1982 |
| EP | 0167300 A1 | 1/1986 |
| EP | 0137749 A2 | 2/1986 |
| EP | 0175558 A1 | 3/1986 |
| EP | 0104197 | 5/1986 |
| EP | 0192587 | 8/1986 |
| EP | 0330853 | 9/1989 |
| EP | 0400904 | 5/1990 |
| EP | 0372847 | 6/1990 |
| EP | 0408528 | 7/1990 |
| EP | 0198682 B1 | 3/1991 |
| EP | 0285420 B1 | 5/1991 |
| EP | 0456647 | 11/1991 |
| EP | 0539274 | 4/1993 |
| EP | 0285786 B1 | 5/1993 |
| EP | 0557786 | 9/1993 |
| EP | 0953560 | 11/1999 |
| EP | 0990638 | 4/2000 |
| EP | 0992482 | 4/2000 |
| EP | 0992484 | 4/2000 |
| EP | 1262234 | 12/2002 |
| EP | 1277826 | 1/2003 |
| EP | 2060553 A1 | 5/2009 |
| EP | 2060555 A1 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 745946 | 3/1956 |
| GB | 1168785 | 10/1969 |
| GB | 1559540 | 1/1980 |
| GB | 2136704 | 9/1984 |
| JP | 4-193304 | 7/1992 |
| JP | 6-116182 | 4/1994 |
| JP | 10-306047 | 11/1998 |
| JP | 11-147845 | 6/1999 |

(56) References Cited

FOREIGN PATENT DOCUMENTS

| | | |
|---|---|---|
| JP | 2001-046874 A | 2/2001 |
| JP | 2001-157841 A | 6/2001 |
| WO | WO 83/03409 A1 | 10/1983 |
| WO | WO 90/07367 | 7/1990 |
| WO | WO 03/040037 | 5/2003 |
| WO | WO 03/106396 | 12/2003 |
| WO | WO 2007/003897 | 1/2007 |
| WO | WO 2008/135192 | 11/2008 |
| WO | WO 2009/009322 A1 | 1/2009 |
| WO | WO 2009/009323 A1 | 1/2009 |
| WO | WO 2009/048335 | 4/2009 |
| WO | WO 2009/063176 A1 | 5/2009 |
| WO | WO 2009/105860 A1 | 9/2009 |
| WO | WO 2010/014145 | 2/2010 |
| WO | WO 2010/014146 | 2/2010 |
| WO | WO 2010/014148 | 2/2010 |
| WO | WO 2010/014151 A1 | 2/2010 |
| WO | WO 2010/014152 | 2/2010 |
| WO | WO 2010/014153 A2 | 2/2010 |
| WO | WO 2010/056299 | 5/2010 |
| WO | WO 2010/055285 | 7/2010 |
| WO | WO 2011/053365 | 5/2011 |
| WO | WO 2011/097194 | 8/2011 |

OTHER PUBLICATIONS

Zheng, et al., (2007). Preparation and catalytic properties of a bimetallic Sn—Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Santori et al., (2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Hilmen, Separation of Azeotropic Mixtures: Tools for Analysis and Studies on Batch Distillation Operation (Nov. 2000) p. 17-20.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

International Search Report and Written Opinion for PCT/US2010/022947 mailed Jun. 7, 2010.

International Search Report for PCT/US2011/023314 dated Aug. 5, 2011 (4 pages).

Zhang et al., Hydrogenation of Ethyl Acetate to Ethanol over Ni-Based Catalysts Obtained from Ni/Al Hydrotalcite-Like Compounds. Molecules 2010, 15, 5139-5152, 2010.

Pestman et al., The formation of ketones and aldehydes from carboxylic acids, structure-activity relationship for two competitive reactions, Journal of Molecular Catalysis A: Chemical 103 Jun. 14, 1995, 175-180.

Pestman et al., Reactions of Carboxylic Acids on Oxides, Journal of Catalysis 168:255-264 (1997).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Proc. Roy Soc. A314, pp. 473-498 (1970).

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Brunauer Emmett and Teller, J. Am. Chem. Soc. 60, 309 (1938).

Ivan Hodac et al., "Ethanol Guidelines", Mar. 1, 2009, pp. 1-12.

International Fuel Quality Center, "Setting a Quality Standard for Fuel Ethanol—DEH Ethanol Standard 18/2004 report", Jan. 1, 2004, pp. 1-56.

Invitation to Pay Additional Fees and Partial Search Report for PCT/US2011/023331 mailed May 4, 2011.

International Search Report and Written Opinion for PCT/US2010/054136 mailed May 25, 2010.

International Search Report and Written Opinion for PCT/US2011/023338 mailed Sep. 6, 2011.

International Search Report for PCT/US2011/023269 mailed Aug. 25, 2011.

International Written Opinion for PCT/US2011/023314 mailed May 15, 2012.

International Preliminary Report on Patentability for PCT/US2011/023314 mailed Jul. 5, 2012.

International Search Report for PCT/US2011/023278 mailed Jul. 18, 2011.

International Search Report and Written Opinion for PCT/US2011/046502 mailed May 21, 2012.

International Written Opinion for PCT/US2011/023278 mailed Jan. 30, 2012.

International Preliminary Report on Patentability for PCT/US2011/023278 mailed May 18, 2012.

International Search Report and Written Opinion for PCT/US2011/023322 mailed Sep. 6, 2011.

Invitation to Pay Fees for PCT/US2011/046502 mailed Mar. 9, 2012.

Waterland, et al., "Safety and Performance Assessment of Ethanol/Diesel Blends (e-blend)", NREL-SR-540-34817, at p. 1-1, 2003.

J. Jones, Platinum Metals Review, vol. 44, No. 3, pp. 94-104 (Jul. 2000).

International Search Report and Written Opinion for PCT/US2011/046493 mailed Apr. 23, 2012.

International Search Report and Written Opinion for PCT/US2011/046500 mailed Feb. 2, 2012.

International Search Report for PCT/US2011/046508 mailed Mar. 29, 2012.

International Search Report for PCT/US2011/046500 mailed Mar. 29, 2012.

Pestman et al., Identification of the Active Sites in the Selective Hydrogenation of Acetic Acid to Acetaldehyde on Iron Oxide Catalysts, Journal of Catalysis 174:142-152 (1998).

* cited by examiner

PROCESSES FOR PRODUCING ANHYDROUS ETHANOL COMPOSITIONS

CROSS REFERENCE TO RELATED APPLICATIONS

This application claims priority to U.S. patent application Ser. No. 12/903,756, filed on Oct. 13, 2010, which claims priority to U.S. Provisional Application No. 61/332,726, filed on May 7, 2010 and to U.S. Provisional Application No. 61/300,815, filed on Feb. 2, 2010, the entire contents and disclosures of which are incorporated herein by reference.

FIELD OF THE INVENTION

The present invention relates generally to processes for producing an anhydrous ethanol composition. In particular, the present invention relates to processes for producing an anhydrous ethanol composition via the hydrogenation of acetic acid.

BACKGROUND OF THE INVENTION

Ethanol is a particularly valuable alcohol that has a broad range of applications such as chemical solvents; feedstocks for various chemical syntheses; consumable products, e.g., beer, wine, and spirits; and fuels.

The hydrogenation of alkanoic acids and/or other carbonyl group-containing compounds is one method of producing alcohols such as ethanol. This method has been widely studied. As a result, a variety of related combinations of reactants, catalysts, supports, and operating conditions have been mentioned in literature.

Anhydrous ethanol, however, is preferred for some ethanol applications, e.g., fuels. Anhydrous or substantially anhydrous ethanol, however, is often difficult to obtain from conventional hydrogenation and separation processes. For example, the ethanol and water produced in conventional hydrogenation reactions may form a binary azeotrope. This azeotrope contains about 95% ethanol and about 5% water. Because the boiling point of this azeotrope (78° C.) is just slightly below that of pure ethanol (78.4° C.), an anhydrous or substantially anhydrous ethanol composition is difficult to obtain from a crude ethanol composition via simple, conventional distillation.

Even though some hydrogenation and separation techniques may be known, the need exists for an improved process and system for producing anhydrous ethanol compositions.

SUMMARY OF THE INVENTION

The present invention is directed to a process for producing anhydrous ethanol compositions. The process comprises the step of hydrogenating acetic acid in the presence of a catalyst to form a crude ethanol product. In one embodiment, the process further comprises the step of separating in a first column at least a portion of the crude ethanol product into a first distillate and a first residue. The first distillate comprises ethanol, water, and ethyl acetate. The first residue comprises acetic acid. The process further comprises the step of separating in a second column at least a portion of the first distillate into a second distillate and a second residue. The first distillate comprises ethyl acetate and the second residue comprises ethanol and water. The process further comprises the step of separating in a third column at least a portion of the second residue into a third distillate and a third residue. The third distillate comprises ethanol and residual water and the third residue comprises separated water. The process further comprises the step of dehydrating at least a portion of the third distillate to form the anhydrous ethanol composition. The anhydrous ethanol composition, as formed, comprises less than 1 wt. % water, e.g., less than 0.5 wt. %, less than 0.1 wt. %, less than 0.01 wt. %, less than 0.001 wt. %, or less than 0.0001 wt. %. In terms of ranges, the anhydrous ethanol composition comprises from 0.0001 wt. % to 1 wt. % water, e.g., from 0.001 wt. % to 0.5 wt. %, or from 0.001 wt. % to 0.05 wt. %. The weight percentages are based on the total weight of the anhydrous ethanol composition. Preferably, the anhydrous ethanol composition formed by the inventive process comprises from 95 wt. % to 99.9999 wt. % ethanol and from 0.0001 wt. % to 1 wt. % water. In one example, the third distillate comprises from 0.0001 wt. % to 12 wt. % water and/or the dehydrating step removes at least 50 wt. % of the water from the third distillate.

Preferably, the dehydrating step comprises separating in a fourth column at least a portion of the third distillate into a fourth distillate and a fourth residue. The fourth distillate comprises the anhydrous ethanol composition and the fourth residue comprises water. In one embodiment, the fourth column is an extractive distillation column comprising from 10 to 100 trays. Preferably, the extractive distillation column comprises at least one extraction agent selected from the group consisting of glycols, glycerol, gasoline, and hexane. In another embodiment, a molecular sieve unit dehydrates the third distillate. In another embodiment, a membrane separation unit dehydrates the third distillate.

In another embodiment, the invention relates to a system for producing anhydrous ethanol compositions. The system comprises a reactor for hydrogenating acetic acid in the presence of a catalyst to form a crude ethanol product. The system further comprises a first column for separating at least a portion of the crude ethanol product into a first distillate and a first residue. The system further comprises a second column for separating at least a portion of the first distillate into a second distillate and a second residue. The system further comprises a third column for separating at least a portion of the second residue into a third distillate and a third residue. The system further comprises a dehydrator for dehydrating at least a portion of the third distillate to form the anhydrous ethanol composition. Exemplary dehydrators include an extractive distillation column, a molecular sieve unit, a membrane separation unit, and combinations thereof.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to processes for producing anhydrous ethanol compositions. In one embodiment, the anhydrous ethanol composition is separated from a crude acetic acid product that is produced via hydrogenation of acetic acid. The hydrogenation may be performed in the presence of a catalyst. The separating may be performed in one or more separation units, e.g., distillation columns, e.g., two or more, or three or more. In a preferred embodiment, the process includes the step of dehydrating an ethanol enriched stream derived from the crude ethanol product to yield the anhydrous ethanol composition. The anhydrous ethanol composition comprises ethanol and less than 1 wt. % water, e.g., less than 0.5 wt. %, less than 0.1 wt. %, less than 0.01 wt. %, less than 0.001 wt. %, or less than 0.0001 wt. %, based on the total weight of the anhydrous ethanol composition. In terms of ranges, depending largely on the dehydration technique employed, the anhydrous ethanol composition may comprise from 0.0001 wt. % to 1 wt. % water, e.g., from 0.001 to 0.5 wt. % or from 0.001 to 0.05 wt. %, based on the total weight of the anhydrous ethanol composition.

Hydrogenation Process

The hydrogenation of acetic acid to form ethanol and water may be represented by the following reaction:

Suitable hydrogenation catalysts include catalysts comprising a first metal and optionally one or more of a second metal, a third metal or additional metals, optionally on a catalyst support. The first and optional second and third metals may be selected from Group IB, IIB, IIIB, IVB, VB, VIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Publication Nos. 2010/0029995 and 2010/0197485, the entireties of which are incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, nium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 wt. % to 10 wt. %, e.g., from 0.1 wt. % to 5 wt. %, or from 0.1 wt. % to 3 wt. %. The second metal preferably is present in an amount from 0.1 wt. % and 20 wt. %, e.g., from 0.1 wt. % to 10 wt. %, or from 0.1 wt. % to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 wt. % and 4 wt. %, e.g., from 0.1 wt. % to 3 wt. %, or from 0.1 wt. % to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O/g$ support, a surface area of about 160 to 175 $m^2/g$, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Publication No. 2010/0029995, and U.S. application Ser. No. 12/698,968, referred to above, the entireties of which are incorporated herein by reference.

Some embodiments of the process of hydrogenating acetic acid to form ethanol according to one embodiment of the invention may include a variety of configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syn gas is diverted from the methanol synthesis loop and supplied to a separator unit to recover carbon monoxide and hydrogen, which are then used to produce acetic acid. In addition to acetic acid, such a process can also be used to make hydrogen which may be utilized in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosures of which are incorporated herein by reference. Optionally, the production of ethanol may be integrated with such methanol carbonylation processes.

U.S. Pat. No. RE 35,377 also incorporated herein by reference, provides a method for the production of methanol by conversion of carbonaceous materials such as oil, coal, natural gas and biomass materials. The process includes hydro gasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas as well as U.S. Pat. No. 6,685,754, the disclosures of which are incorporated herein by reference.

In one optional embodiment, the acetic acid feed stream fed to the hydrogenation reaction comprises acetic acid and may also comprise other carboxylic acids, e.g., propionic acid, esters, and anhydrides, as well as acetaldehyde and acetone. In one embodiment, the acetic acid fed to the hydrogenation reaction comprises propionic acid. For example the propionic acid in the acetic acid feed stream may range from 0.001 wt. % to 15 wt. %, e.g., from 0.001 wt. % to 0.1 wt. %, from 0.125 wt. % to 12.5 wt. %, from 1.25 wt. % to 11.25 wt. %, or from 3.75 wt. % to 8.75 wt. %. Thus, the acetic acid feed stream may be a cruder acetic acid feed stream, e.g., a less-refined acetic acid feed stream.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature. Following the vaporization, the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 or at least 600 grams, is preferred. In terms of ranges, the productivity preferably is from 200 to 3,000 grams of ethanol per kilogram catalyst per hour, e.g., from 400 to 2,500 or from 600 to 2,000.

In various embodiments, the crude ethanol product produced by the hydrogenation process, before any subsequent processing, such as purification and separation, will typically comprise unreacted acetic acid, ethanol, and water. As used herein, the term "crude ethanol product" refers to any composition comprising from 5 wt. % to 70 wt. % ethanol and from 5 wt. % to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol, or at least 20 wt. % ethanol.

The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably present in amounts from 0 wt. % to 90 wt. %, e.g., from 5 wt. % to 80 wt. %, from 15 wt. % to 70 wt. %, from 20 wt. % to 70 wt. % or from 25 wt. % to 65 wt. %. As water is formed in the reaction process, the crude ethanol product will generally comprise water, for example, in amounts ranging from 5 wt. % to 35 wt. %, e.g., from 10 wt. % to 30 wt. % or from 10 wt. % to 26 wt. %. Ethyl acetate may also be produced during the hydrogenation of acetic acid or through side reactions. In these embodiments, the crude ethanol product comprises ethyl acetate in amounts ranging from 0 wt. % to 20 wt. %, e.g., from 0 wt. % to 15 wt. %, from 1 wt. % to 12 wt. % or from 3 wt. % to 10 wt. %. Acetaldehyde may also be produced through side reactions. In these embodiments, the crude ethanol product comprises acetaldehyde in amounts ranging from Q wt. % to 10 wt. %, e.g., from 0 wt. % to 3 wt. %, from 0.1 wt. % to 3 wt. % or from 0.2 wt. % to 2 wt. %.

Other components, such as, for example, esters, ethers, aldehydes, ketones, alkanes, and carbon dioxide, if detectable, collectively may be present in amounts less than 10 wt. %, e.g., less than 6 wt. %, or less than 4 wt. %. In terms of ranges, the crude ethanol composition may comprise the other components in an amount from 0.1 wt. % to 10 wt. %, e.g., from 0.1 wt. % to 6 wt. %, or from 0.1 wt. % to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

Purification

Figure 1A:
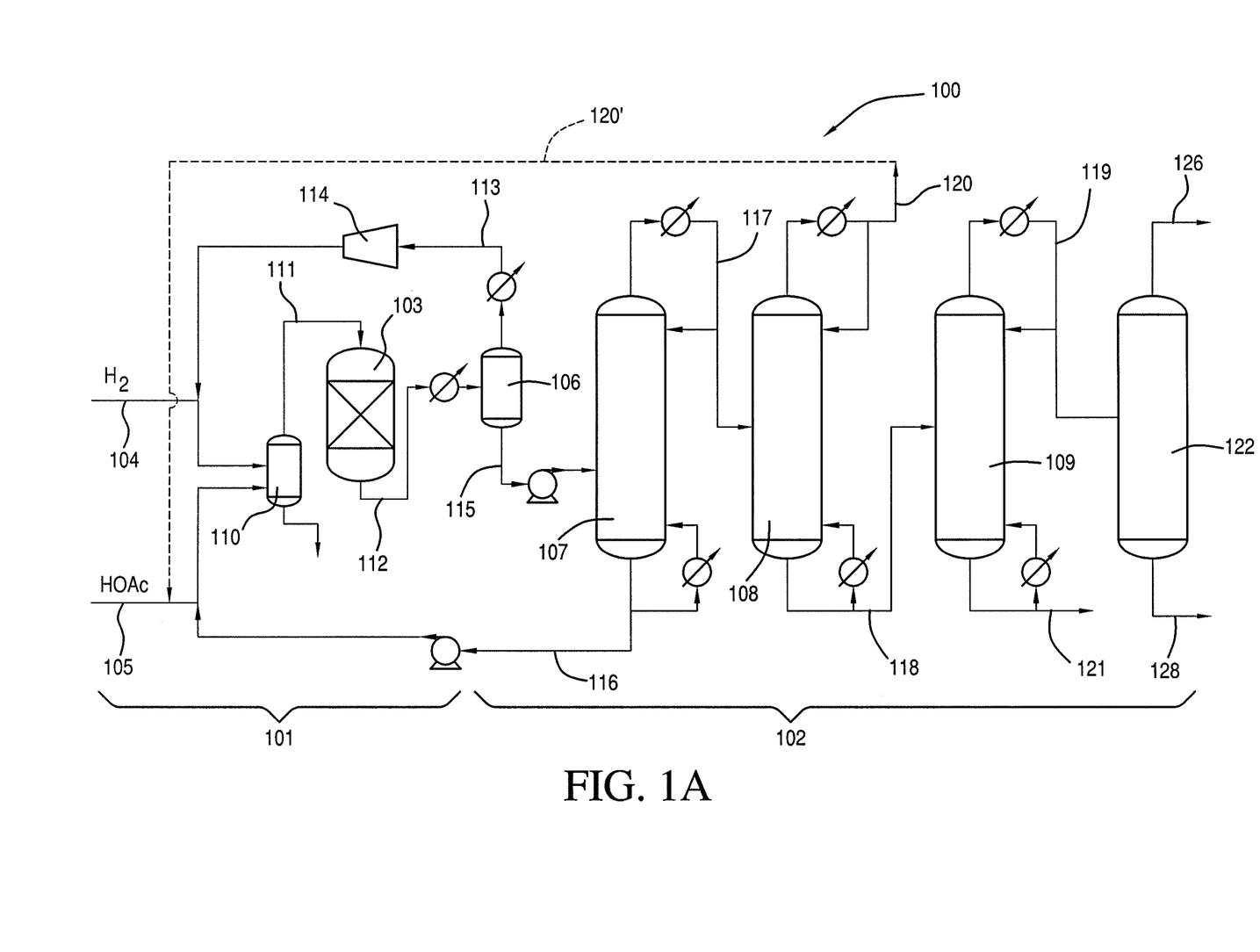
FIG. 1A is a schematic diagram of a hydrogenation system having a fourth column in accordance with one embodiment of the present invention.
Figure 1B:
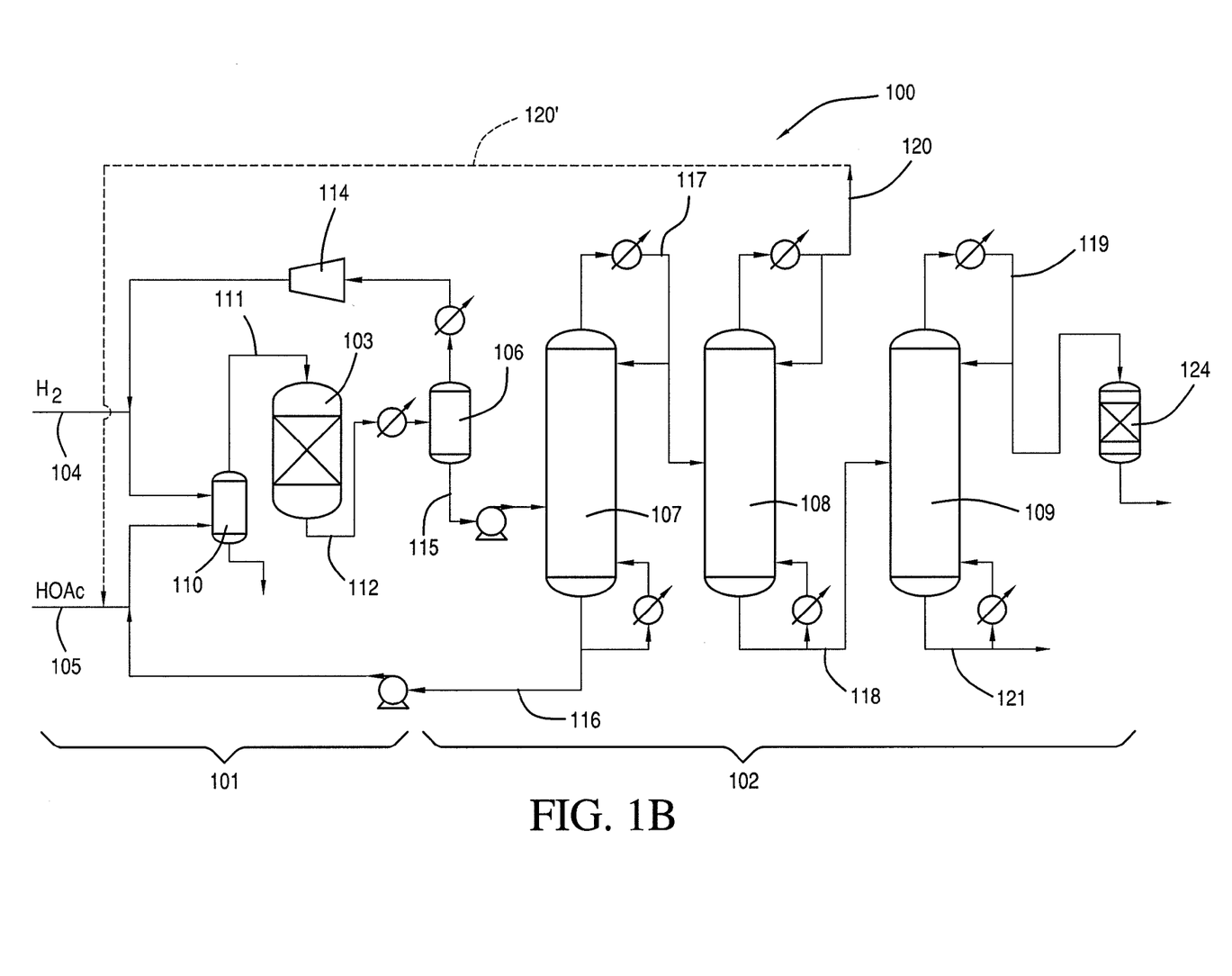
FIG. 1B is a schematic diagram of a hydrogenation system having a molecular sieve unit in accordance with one embodiment of the present invention.

FIGS. 1A and 1B show a hydrogenation system 100 suitable for the hydrogenation of acetic acid and the separation of an anhydrous ethanol composition from the crude reaction mixture according to one embodiment of the invention. System 100 comprises reaction zone 101 and distillation zone 102. Reaction zone 101 comprises reactor 103, hydrogen feed line 104 and acetic acid feed line 105. In FIG. 1A, distillation zone 102 comprises flasher 106, first column 107, second column 108, third column 109, and fourth column 122. In FIG. 1B distillation zone 102 comprises flasher 106, first column 107, second column 108, third column 109, and molecular sieve unit 124. Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1A, and may be recycled thereto. In addition, although FIG. 1A shows line 111 being directed to the top of reactor 103, line 111 may be directed to the side, upper portion, or bottom of reactor 103.

Reactor 103 contains the catalyst used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106, in one embodiment, preferably operates at a temperature of from 50° C. to 500° C., e.g., from 70° C. to 400° C. or from 100° C. to 350° C. In one embodiment, flasher 106 operates at a pressure ranging from 50 KPa to 2000 KPa, e.g., from 75 KPa to 1500 KPa or from 100 to 1000 KPa. In one preferred embodiment, the temperature and pressure of flasher 106 is similar to the temperature and pressure of reactor 103.

The vapor stream exiting the flasher 106 may comprise hydrogen and hydrocarbons, which may be purged and/or returned to reaction zone 101 via line 113. As shown in FIG. 1A, the returned portion of the vapor stream passes through compressor 114 and is combined with the hydrogen feed and co-fed to vaporizer 110.

The liquid from flasher 106 is withdrawn and pumped as a feed composition via line 115 to the side of first column 107, also referred to as the acid separation column. The contents of line 115 typically will be substantially similar to the product obtained directly from the reactor, and may, in fact, also be characterized as a crude ethanol product. However, the feed composition in line 115 preferably has substantially no hydrogen, carbon dioxide, methane or ethane, which are removed by flasher 106. Exemplary components of liquid in line 115 are provided in Table 2. It should be understood that liquid line 115 may contain other components, not listed, such as components in the feed.

TABLE 2

FEED COMPOSITION

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 35 | 5 to 30 | 10 to 30 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may advantageously comprise propanol, e.g., isopropanol and/or n-propanol, in small amounts, e.g., from 0.001 wt. % to 0.1 wt. %, from 0.001 wt. % to 0.05 wt. % or from 0.001 wt. % to 0.03 wt. %. As a result of the low concentration of these other alcohols in the feed composition, the resultant anhydrous ethanol composition advantageously comprises the alcohols, if at all, only in trace amounts (see discussion below). These trace amounts are significantly lower than those levels obtained via methods that do not utilize the hydrogenantion of acetic acid. It should be understood that these other components may be carried through in any of the distillate or residue streams described herein.

When the content of acetic acid in line 115 is less than 5 wt. %, the acid separation column 107 may be skipped and line 115 may be introduced directly to second column 108, also referred to herein as a light ends column.

In the embodiment shown in FIG. 1A, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108, or 109 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1A and 1B. As shown in FIGS. 1A and 1B, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIGS. 1A and 1B, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependant on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa.

Exemplary distillate and residue compositions for first column 107 are provided in Table 3 below. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| FIRST COLUMN | | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below.

$$EtOH+HOAc \leftrightarrows EtOAc+H_2O$$

In the event the crude ethanol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increases from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

In addition, it has now been discovered that the above-described equilibrium reaction may also favor ethanol formation in the top region of first column 107.

The distillate, e.g., overhead stream, of column 107 optionally is condensed and refluxed as shown in FIG. 1A, preferably, at a reflux ratio of 1:5 to 10:1. The distillate in line 117 preferably comprises ethanol, ethyl acetate, and water, along with other impurities, which may be difficult to separate due to the formation of binary and tertiary azeotropes. The first distillate also comprises a significantly reduced amount of acetic acid.

The first distillate in line 117 is introduced to the second column 108, also referred to as the "light ends column," preferably in the middle part of column 108, e.g., middle half or middle third. As one example, when a 25 tray column is utilized in a column without water extraction, line 117 is introduced at tray 17. Second column 108 may be a tray column or packed column. In one embodiment, second column 108 is a tray column having from 5 to 70 trays, e.g., from 15 to 50 trays or from 20 to 45 trays.

In one embodiment, the second column 108 may be an extractive distillation column. In such embodiments, an extraction agent, such as water, may be added to second column 108. If the extraction agent comprises water, it may be obtained from an external source or from an internal return/recycle line from one or more of the other columns. In a preferred embodiment, the water in the third residue of third column 109 is utilized as the extraction agent.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary components for the distillate and residue compositions for second column 108 are provided in Table 4 below. It should be understood that the distillate and residue may also contain other components, not listed, such as components in the feed.

TABLE 4

SECOND COLUMN

|  | Conc. (wt. %) | Conc. (wt. %) | Conc. (wt. %) |
| --- | --- | --- | --- |
| Distillate |  |  |  |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero.

The second distillate in line 120 preferably is refluxed as shown in FIG. 1A, for example, at a reflux ratio of from 1:10 to 10:1, e.g., from 1:5 to 5:1 or from 1:3 to 3:1. The distillate from second column 108 may be purged. In one embodiment, since the second distillate contains ethyl acetate, all or a portion of the distillate from second column 108 may be recycled to reaction zone 101 via optional line 120' in order to convert the ethyl acetate to additional ethanol. As shown in the FIGS., all or a portion the distillate may be recycled to reactor 103 via optional line 120', and may be co-fed with the acetic acid feed line 105. In another embodiments, the second distillate in line 120 may be further purified to remove impurities, such as acetaldehyde, using one or more additional columns (not shown).

As shown, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown in FIG. 1A, for example, at a reflux ratio of from 1:10 to 10:1, e.g., from 1:3 to 3:1 or from 1:2 to 2:1. The third residue in line 121, which preferably comprises primarily water, preferably is removed from the system 100 or may be partially returned to any portion of the system 100. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C., when the column is operated at atmospheric pressure. Exemplary distillate and residue compositions for third column 109 are provided in Table 5 below. It should be understood that the distillate and residue may also contain other components, not listed, such as components in the feed.

TABLE 5

THIRD COLUMN

| | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108, and/or 109 in system 100. In one embodiment, at least one side stream may be used to remove impurities from the third column 109. The impurities may be purged and/or retained within the system 100.

As discussed above, the third distillate in line 119 preferably is further processed to substantially remove water therefrom. The further processing results in the formation of an anhydrous ethanol product stream, e.g., anhydrous ethanol composition. In one embodiment, the further processing employs one or more separation units, e.g., dehydrators. Examples of suitable dehydrators include an extractive distillation column 122 (as shown in FIG. 1A); a molecular sieve unit 124 (as shown in FIG. 1B); and/or a desiccant (not shown). For example, useful dehydration methods and/or units include those discussed in U.S. Pat. Nos. 4,465,875; 4,559,109; 4,654,123; and 6,375,807. The entireties of these patents are hereby incorporated by reference.

Typically, the water and the ethanol in the third distillate form a water/ethanol azeotrope. In one embodiment, the dehydrators of the present invention remove the water from the water/ethanol azeotrope in the third distillate. For example, the dehydration may remove at least 50 wt. % of the water from the third distillate, e.g., at least 75 wt. %, at least 90 wt. %, at least 95 wt. %, or at least 99 wt. %. In terms of ranges, the dehydration removes from 50 wt. % to 100 wt. % of the water from the third distillate, e.g., from 75 wt. % to 99.9999 wt. %, from 90 wt. % to 99.999 wt. %, from 90 wt. % to 99.99 wt. %, from 90 wt. % to 99.9 wt. %, or from 90 wt. % to 99.5 wt. %. The removal of this water from the third distillate results in the formation of the anhydrous ethanol composition.

Water-containing stream 128 exiting the dehydrator(s) comprises primarily water, e.g., at least 50 wt. % water, e.g., at least 75 wt. %, at least 90 wt. %, at least 95 wt. %, or at least 99 wt. %, and preferably is removed from system 100. In one embodiment, the fourth residue 128 may be partially returned to any portion of system 100. In a preferred embodiment, the water may be utilized as an extraction agent in any one of the columns, e.g., second column 108.

In FIG. 1A, the distillate from third column 109, which comprises ethanol/water azeotrope, may be fed, e.g., via line 119, to fourth column 122, also referred to as the "finishing column." Fourth column 122 further separates, e.g., distills, water from the water/ethanol azeotrope in the third distillate. As a result, fourth column 122 recovers ethanol that has been further dehydrated as the fourth distillate in line 126.

Preferably, fourth column 122 is an extractive distillation column that employs an extraction agent and preferably operates at atmospheric pressure. Extractive distillation is a vapor-liquid separation process, which uses an additional component to increase the relative volatility of the components to be separated. In extractive distillation, a selective high boiling solvent is utilized to alter the activity coefficients and, hence, increase the separation factor of the components. The additional component may be a liquid solvent, an ionic liquid, a dissolved salt, a mixture of volatile liquid solvent and dissolved salt, or hyperbranched polymer.

Fourth column 122 preferably comprises from 1 to 150 trays, e.g., from 10 to 100 or from 20 to 70 trays. As indicated above, the trays may be sieve trays, fixed valve trays, movable valve trays, or any other suitable design known in the art. Exemplary extraction agents may include, but are not limited to glycols, glycerol, gasoline, and hexane. The third distillate in line 119 may be introduced to fourth column 122 at any level. Preferably, line 119 is introduced into the fourth column 122 in the middle part of fourth column 122, e.g., the middle half or middle third.

In one embodiment, as shown in FIG. 1B, the distillate from third column 109 is fed to a molecular sieve unit 124 comprising molecular sieves. In these embodiments, the molecular sieves separate additional water from the third distillate in line 119. In some embodiments, molecular sieve unit 124 may be used in place of or in conjunction with the finishing column. Generally speaking, the molecular sieves may be configured in a molecular sieve bed (not shown). In one embodiment, the molecular sieves are selected to remove one or more impurities that may exist in the third distillate. The selection criteria may include, for example, pore size and volume characteristics. In one embodiment, the molecular sieve material is selected to remove water, acetic acid, and/or ethyl acetate from the third distillate to form the anhydrous ethanol composition. Suitable molecular sieves include, for example, zeolites and molecular sieves 3A, 4A and 5A (commercially available from Aldrich). In another embodiment, an inorganic adsorbents such as lithium chloride, silica gel, activated alumina, and/or bio-based adsorbents such as corn grits, may be utilized. In a preferred embodiment, molecular sieve unit 124 removes water from the third distillate in the amounts discussed above.

In addition, other separation units, e.g., dehydrating units, such as desiccant systems and/or membrane systems, may be used, either in place of or in conjunction with the finishing column and/or the molecular sieve unit discussed above. If multiple dehydrating units are utilized, the dehydrating units, being of the same or of different type, may be utilized in any configuration. Preferably, an extractive distillation column and a membrane system are utilized with one another. Optionally, the molecular sieves are employed in a bed within the finishing column, e.g., at the upper portion thereof.

Other exemplary dehydration processes include azeotropic distillation and membrane separation. In azeotropic distillation, a volatile component, often referred to as an entrainer, is added to the components to be separated. The addition of the entrainer forms an azeotrope with the components, thus changing the relative volatilities thereof. As a result, the separation factors (activity coefficients) of the components are improved. The azeotropic distillation system, in one embodiment, comprises one or more distillation columns, e.g., two or more or three or more.

Membrane separation, e.g., membrane pervaporation, may also be an effective and energy-saving process for separating azeotropic mixtures. Generally speaking, pervaporation is based on the solution-diffusion mechanism, which relies on the gradient of the chemical potential between the feed and the permeate sides of the membrane. The membranes, in one embodiment, may be hydrophilic or hydrophobic. Preferably, the membranes are hydrophilic or water permselective due to the smaller molecular size of water. In other embodiments, the membranes are hydrophobic or ethanol permselective. Typically, there are three categories of membranes that may be used—inorganic, polymeric, and composite membrane.

Anhydrous Ethanol Composition

The anhydrous ethanol compositions beneficially comprise ethanol and, if any, a small amount of water preferably formed via the inventive acetic acid hydrogenation and separation steps. In one embodiment, the term "anhydrous ethanol composition," as used herein, means a substantially anhydrous ethanol composition. For example a substantially anhydrous ethanol composition may have a water content of less than 1 wt. % water, e.g., less than 0.5 wt. %, less than 0.1 wt. %, less than 0.01 wt. %, less than 0.001 wt. %, or less than 0.0001 wt. %, based on the total weight of the substantially anhydrous ethanol composition. Table 6 provides exemplary ranges for the water concentration in the anhydrous ethanol compositions. Although Table 6 indicated that water is preferably present in a small amount, in other embodiments, the anhydrous ethanol composition may be completely anhydrous, e.g., containing no detectable water. In these cases conventional water detection methods employed in the industry may be utilized to measure water content or lack thereof. Preferably, the anhydrous ethanol composition comprises at least 95 wt. % ethanol, e.g., at least 95 wt. %, at least 99 wt. %, at least 99.9 wt. %, or at least 99.99 wt. %. Table 6 provides exemplary ranges for the ethanol concentration in the anhydrous ethanol compositions.

In addition to the ethanol and, if any, a small amount of water, the anhydrous ethanol composition may also comprise only trace amounts of other impurities such as acetic acid; $C_3$ alcohols, e.g., n-propanol; and/or $C_4$-$C_5$ alcohols. Exemplary compositional ranges for the ethanol, the water, and various impurities that may be present in small amounts, if at all, are provided below in Table 6.

TABLE 6

ANHYDROUS ETHANOL COMPOSITIONS

| Component | Conc. (wt. %) | Conc. (wt. %) | Conc. (wt. %) |
|---|---|---|---|
| Ethanol | 95 to 100 | 95 to 99.99 | 99 to 99.90 |
| Water | 0.0001 to 1 | 0.001 to 0.5 | 0.001 to 0.05 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The anhydrous ethanol compositions of the present invention preferably contain very low amounts, e.g., less than 0.5 wt. %, of other alcohols, such as methanol, butanol, isobutanol, isoamyl alcohol and other $C_4$-$C_{20}$ alcohols.

The anhydrous ethanol compositions of the embodiments of the present invention may be suitable for use in a variety of applications including fuels, solvents, chemical feedstocks, pharmaceutical products, cleansers, sanitizers, or hydrogenation transport. In fuel applications, the anhydrous ethanol composition may be blended with gasoline for motor vehicles such as automobiles, boats and small piston engine aircrafts. In non-fuel applications, the anhydrous ethanol composition may be used as a solvent for toiletry and cosmetic preparations, detergents, disinfectants, coatings, inks, and pharmaceuticals. The anhydrous ethanol composition may also be used as a processing solvent, e.g., in manufacturing processes for medicinal products, food preparations, dyes, photochemicals and latex processing.

The anhydrous ethanol composition may also be used as a chemical feedstock to make other chemicals such as vinegar, ethyl acrylate, ethyl acetate, ethylene, glycol ethers, ethylamines, aldehydes, and higher alcohols, especially butanol. The anhydrous ethanol composition may be suitable for use as a feed stock in esters production. Preferably, in the production of ethyl acetate, the anhydrous ethanol composition may be esterified with acetic acid or reacted with polyvinyl acetate. The anhydrous ethanol composition may be dehydrated to produce ethylene. Any of known dehydration catalysts can be employed to dehydrate ethanol, such as those described in copending U.S. Pub. 20100030001 and 20100030002, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

EXAMPLES

Example 1

Crude ethanol product samples were prepared via acetic acid hydrogenation as discussed above. The samples comprised ethanol, acetic acid, acetaldehyde, water, and ethyl acetate.

Each of the crude ethanol product samples was purified using first, second, and third columns as shown in FIG. 1A. In each case, the third distillate, yielded from the respective crude ethanol product sample, was analyzed. The average compositional values of the third distillate are provided in Table 7.

TABLE 7

| Component | Third Distillate (avg. wt. %) |
|---|---|
| Ethanol | 92.27 |
| Water | 7.7 |
| Ethyl Acetate | 0.008 |
| Acetaldehyde | 0.0002 |
| Acetic Acid | 0.0001 |
| Isopropanol | 0.0118 |
| N-propanol | 0.0127 |
| Acetone | 0 |
| Acetal | 0.0001 |

The third distillates, when dehydrated as discussed above, provide for anhydrous ethanol compositions having the average compositional values are provided in Table 8. As shown in Table 8, the anhydrous ethanol compositions that may be formed via the inventive acetic acid hydrogenation and separation steps, comprise ethanol and, if any, a small amount of water.

TABLE 8

| Component | Anhydrous Ethanol Compositions (avg. wt. %) |
|---|---|
| Ethanol | 99.46 |
| Water | 0.50 |
| Ethyl Acetate | 0.009 |
| Acetaldehyde | 0.0002 |
| Acetic Acid | 0.0001 |
| Isopropanol | 0.0127 |
| N-propanol | 0.0131 |
| Acetone | 0 |
| Acetal | 0.0001 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A system for producing an anhydrous ethanol composition, the system comprising:
    a reactor for hydrogenating acetic acid in the presence of a catalyst to form a crude ethanol product;
    a first column for separating at least a portion of the crude ethanol product into a first distillate comprising ethanol, water and ethyl acetate, and a first residue comprising acetic acid;
    a second column for separating at least a portion of the first distillate into a second distillate comprising ethyl acetate and a second residue comprising ethanol and water;
    a third column for separating at least a portion of the second residue into a third distillate comprising ethanol and water and a third residue comprising water; and
    a dehydrator for dehydrating at least a portion of the third distillate to form the anhydrous ethanol composition.

2. The system of claim 1, wherein the anhydrous ethanol composition comprises less than 1 wt. % water.

3. The system of claim 1, wherein the anhydrous ethanol composition comprises less than 0.1 wt. % water.

4. The system of claim 1, wherein the dehydrator comprises a fourth column.

5. The system of claim 4, wherein the fourth column comprises an extractive distillation column that employs at least one extraction agent selected from the group consisting of glycols, glycerol, gasoline, and hexane.

6. The system of claim 1, wherein the dehydrator comprises a molecular sieve unit comprising a molecular sieve.

7. The system of claim 1, wherein the catalyst comprises a first metal selected from the group consisting of copper, cobalt, nickel, ruthenium, rhodium, osmium, iridium, platinum, titanium, zinc, chromium, rhenium, molybdenum, and tungsten.

8. The system of claim 1, wherein the crude ethanol product comprises at least 10 wt. % ethanol.

9. A system for producing an anhydrous ethanol composition, the system comprising:
    a reactor for hydrogenating acetic acid in the presence of a catalyst to form an ethanol product;
    a light ends column for separating at least a portion of the ethanol product into a first distillate comprising ethyl acetate, and a first residue comprising ethanol and water;
    a product column for separating at least a portion of the first residue into a second distillate comprising ethanol and residual water and a second residue comprising separated water; and
    a dehydrator for dehydrating at least a portion of the second distillate to form the anhydrous ethanol composition.

10. The system of claim 9, further comprising a flasher for flashing the ethanol product to form the at least a portion of the ethanol product.

11. The system of claim 9, wherein the anhydrous ethanol composition comprises less than 1 wt. % water.

12. The system of claim 9, wherein the anhydrous ethanol composition comprises less than 0.1 wt. % water.

13. The system of claim 9, wherein the dehydrator comprises a fourth column.

14. The system of claim 13, wherein the dehydrator comprises an extractive distillation column that employs at least one extraction agent selected from the group consisting of glycols, glycerol, gasoline, and hexane.

15. The system of claim 9, wherein the dehydrator comprises a molecular sieve unit comprising a molecular sieve.

16. The system of claim 15, wherein the catalyst further comprises a second metal selected from the group consisting of copper, molybdenum, tin, chromium, cobalt, vanadium, tungsten, platinum, lanthanum, cerium, manganese, ruthenium, rhenium, gold, and nickel.

17. The system of claim 9, wherein the catalyst comprises a first metal selected from the group consisting of copper, cobalt, nickel, ruthenium, rhodium, osmium, iridium, platinum, titanium, zinc, chromium, rhenium, molybdenum, and tungsten.

18. The system of claim 17, wherein the catalyst further comprises a second metal selected from the group consisting of copper, molybdenum, tin, chromium, cobalt, vanadium, tungsten, platinum, lanthanum, cerium, manganese, ruthenium, rhenium, gold, and nickel.

19. The system of claim 9, wherein the crude ethanol product comprises at least 10 wt. % ethanol.

* * * * *